United States Patent [19]

Makabe et al.

[11] 4,393,058
[45] Jul. 12, 1983

[54] CEPHALOSPORIN COMPOUNDS

[75] Inventors: Osamu Makabe, Tokyo; Yasushi Murai, Yokosuka; Tuneo Okonogi; Masahiro Onodera, both of Yokohama; Yoshiyuki Koyama, Naka; Takashi Yoshida, Tokyo, all of Japan

[73] Assignee: Meiji Seika Kaisha, Ltd., Tokyo, Japan

[21] Appl. No.: 188,417

[22] Filed: Sep. 18, 1980

[30] Foreign Application Priority Data

Sep. 18, 1979 [JP] Japan .................. 54-118788

[51] Int. Cl.³ .................. C07D 501/36; A61K 31/545
[52] U.S. Cl. ...................... 424/246; 544/27
[58] Field of Search ............. 424/246; 544/27, 21

[56] References Cited

U.S. PATENT DOCUMENTS

| | | | |
|---|---|---|---|
| 4,156,724 | 5/1979 | Yamada et al. | 544/27 |
| 4,258,184 | 3/1981 | Kai et al. | 544/27 |
| 4,294,827 | 10/1981 | Preiss et al. | 544/27 |
| 4,302,454 | 11/1981 | Yamada et al. | 544/27 |
| 4,316,898 | 2/1982 | Wetzet et al. | 544/27 |

Primary Examiner—Nicholas S. Rizzo
Attorney, Agent, or Firm—Sughrue, Mion, Zinn, Macpeak & Seas

[57] ABSTRACT

Cephalosporin compounds, intermediate compounds therefor, and processes for preparation thereof are described; the compounds have the formula (I)

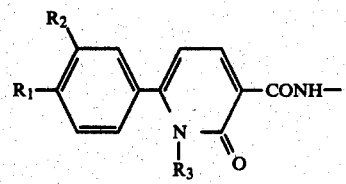

-continued

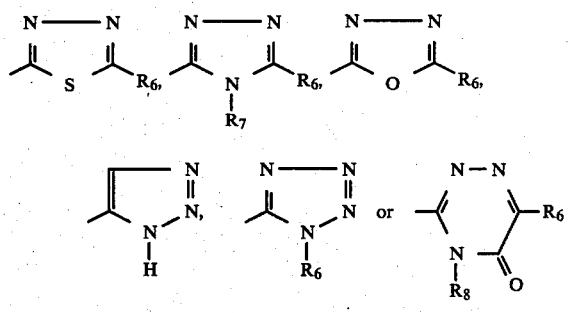

wherein $R_1$ and $R_2$ can each represent hydrogen, a hydroxyl group, a lower alkoxy group, or a substituted or unsubstituted phenylalkoxy group; $R_3$ represents hydrogen or a lower alkyl group; $R_4$ represents hydrogen or a hydroxyl group; and $R_5$ represents

[structures of heterocyclic groups]

wherein $R_6$ is hydrogen, a lower alkyl group, an aminoalkyl group, an aminoaralkyl group, a $-(CH_2)_n-SO_3Na$ group, or a $-(CH_2)_n-COR_9$ group [wherein $R_9$ is a hydroxyl group, an OM group (wherein M is an alkali metal), an alkoxy group, or an

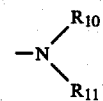

group, (wherein $R_{10}$ and $R_{11}$, which may be the same or different, can represent hydrogen or an alkyl group), and n is 0 or an integer of from 1 to 4]; $R_7$ is hydrogen, a lower alkyl group, an amino group, or a substituted or unsubstituted aryl group; and $R_8$ represents hydrogen or a lower alkyl group; or, a pharmaceutically acceptable salt thereof.

3 Claims, No Drawings

CEPHALOSPORIN COMPOUNDS

BACKGROUND OF THE INVENTION

1. Field of the Invention

This invention relates to novel cephalosporin compounds and pharmaceutically acceptable salts thereof, and to a process for preparing such compounds and salts. More particularly, the invention relates to cephalosporin compounds of the following formulas (I) and (II), or pharmaceutically acceptable salts thereof, and to processes for preparing such compounds or salts.

2. Description of the Prior Art

Cephalosporin type compounds have antibacterial activities and many derivatives thereof have been produced hitherto.

Some of the cephalosporin compounds such as cephalotin, cephalexin, cefazolin, cephaloridine, etc., are used therapeutically as an excellent antibacterial agent.

Recently, a research on cephalosporin compounds aims to develop a useful compound against Gram-negative bacteria, especially *Pseudomonas aeruginosa*, and bacteria which have a lactamase. However, very few cephalosporin compounds exhibit satisfactory antibacterial activity against said bacteria.

Resembled compounds of this invention are disclosed in *Journal of Antibiotics*, Vol. 32, No. 6, page 621 (1979), but do not exhibit satisfactory antibacterial activity against said bacteria.

SUMMARY OF THE INVENTION

One object of this invention is to provide a cephalosporin compound of the formula (I)

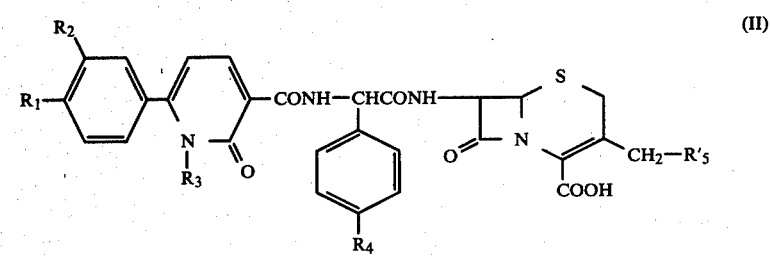

(I)

wherein $R_1$ and $R_2$, which may be the same or different, can represent hydrogen, a hydroxyl group, a lower alkoxy group, or a substituted or unsubstituted phenylalkoxy group; $R_3$ is hydrogen or a lower alkyl group; $R_4$ represents hydrogen or a hydroxyl group; and $R_5$ represents

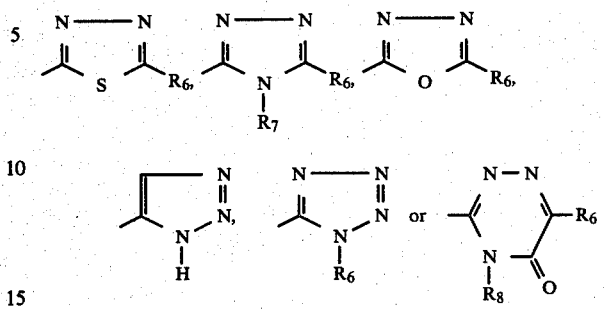

wherein $R_6$ is hydrogen, a lower alkyl group, an aminoalkyl group, an aminoaralkyl group, a $-(CH_2)_n-SO_3Na$ group, or a $-(CH_2)_n-COR_9$ group [wherein $R_9$ is a hydroxyl group, an OM group (wherein M is an alkali metal), an alkoxy group or an

group (wherein $R_{10}$ and $R_{11}$, which may be the same or different, can represent hydrogen or an alkyl group); and n is 0 or an integer of from 1 to 4]; $R_7$ is hydrogen a lower alkyl group, an amino group or a substituted or unsubstituted aryl group; $R_8$ is hydrogen or a lower alkyl group; or, a pharmaceutically acceptable salt thereof.

Another object of this invention is to provide a cephalosporin compound of the formula (II)

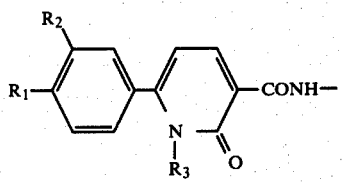

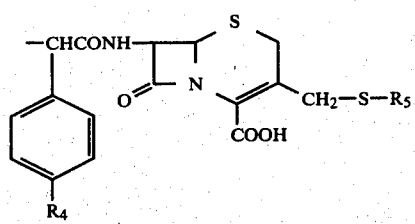

(II)

wherein $R_1$, $R_2$, $R_3$ and $R_4$ have the same meaning as defined above, $R_5'$ represents hydrogen or a lower alkanoyloxy group, or a pharmaceutically acceptable salt thereof.

A further object of this invention is to provide processes for preparing cephalosporin compounds according to the formulae (I) and (II).

DETAILED DESCRIPTION OF THE INVENTION

In the formulae (I) and (II), $R_1$ and $R_2$, which may be the same or different, can represent hydrogen, a hydroxyl group, a lower alkoxy group having from 1 to 5 carbon atoms (such as methoxy, etc.), or a substituted or unsubstituted phenylalkoxy group (where the alkoxy moiety has from 1 to 3 carbon atoms and the substituent includes a hydroxy group or a lower alkoxy group having from 1 to 5 carbon atoms) (such as phenylmethoxy, dimethoxybenzyloxy, etc).

In the formulae (I) and (II), $R_3$ represents hydrogen or a lower alkyl group having from 1 to 5 carbon atoms; and $R_4$ represents hydrogen or a hydroxyl group.

In the formula (I), $R_5$ represents

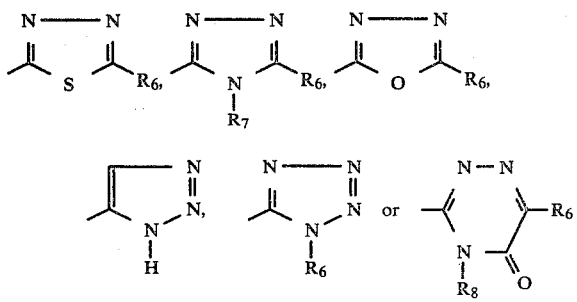

wherein $R_6$ is hydrogen, a lower alkyl group having from 1 to 4 carbon atoms, an aminoalkyl group having from 1 to 4 carbon atoms, an aminoaralkyl group having from 7 to 10 carbon atoms, a $-(CH_2)_n-SO_3Na$ group, or a $-(CH_2)_n-COR_9$ group [wherein $R_9$ is a hydroxyl group, an $-OM$ group (wherein M is an alkali metal), an alkoxy group having from 1 to 5 carbon atoms, or an

group (wherein $R_{10}$ and $R_{11}$, which may be the same or different, can represent hydrogen, or an alkyl group having from 1 to 5 carbon atoms), and n is 0 or an integer of from 1 to 4]; $R_7$ is hydrogen, a lower alkyl group having from 1 to 5 carbon atoms, an amino group or a substituted or unsubstituted aryl group having from 6 to 10 carbon atoms; and $R_8$ is hydrogen or a lower alkyl group having from 1 to 5 carbon atoms.

In the formula (II), $R_5'$ represents hydrogen, or a lower alkanoyloxy group having from 2 to 6 carbon atoms.

Examples of the pharmaceutically acceptable salts of the cephalosporin compounds of the formulae (I) and (II) are alkali metal salts such as sodium salt and potassium salt and various amine salts such as triethylamine.

The compounds of the formulae (I) and (II) of this invention can be prepared by various methods, as illustrated below.

Particularly, a process is provided for preparing a compound of the formula (II)

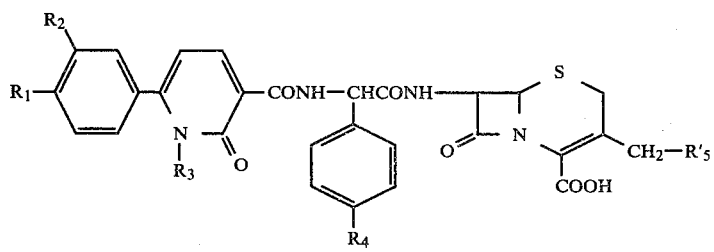

wherein $R_1$, $R_2$, $R_3$, $R_4$ and $R_5'$ each has the same meaning as defined above, wherein a compound of the formula (III)

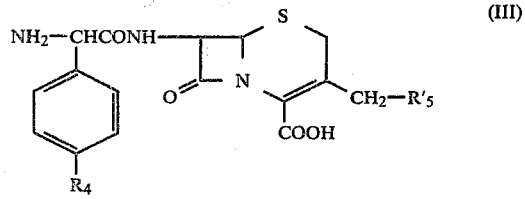

wherein $R_4$ and $R_5'$ each has the same meaning as defined above, or a compound wherein the functional group (i.e., carboxyl group) of the compound of the formula (III) are protected, is reacted with a compound of the formula (IV)

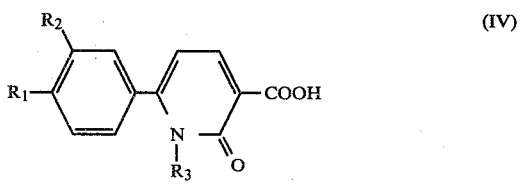

wherein $R_1$, $R_2$ and $R_3$ each has the same meaning as defined above, or a compound wherein some or all of the functional groups (e.g., hydroxyl groups being present in $R_1$ and $R_2$) of the compound of the formula (IV) are protected.

The method described above involves the formation of a $-CONH$-bond (peptide bond) by subjecting the carboxyl group of the compound of the formula (IV) and the amino group of the compound of the formula (III) to dehydration condensation. This type of reaction is commonly employed for synthesizing polypeptides or acylating the amino group at the 6- and 7-positions of penicillin and cephalosporin compounds. In the method of this invention, a derivative including a reactive substituent on the carboxyl group of the compound of the formula (IV) may also be used. Common examples of such reactive derivative include acid halides (e.g., an acid chloride), mixed acid anhydrides of organic acids (e.g., carboxylic acid) and inorganic acids (e.g., sulfuric acid and phosphoric acid), "active esters" having electron attractive alcohol residues or phenol residues, active thioesters, active amides, and "pseudo halogenides" such as acid azide and sulfonate. Various types of dehydration condensing agents that can be employed for forming the desired peptide bond after forming active derivatives at carboxyl group or derivatives having an activated amino group. For example, carbodiimides, alkoxyacetylene, Woodward's reagent, phosphoric acid amide or phosphoric cyanide reagents, phosphite esters and phosphorous anhydrides, pyrophosphate ester reagents, phosphite ester halides, phosphorous halides and other dehydrating agents that are commonly employed in the art may be used. These reagents may be reacted with an amino compound to be acylated together with carboxylic acid in the presence or absence of a base. In the peptide bond forming reaction, a solvent such as water, organic solvent containing or not containing water, or an aprotic organic solvent is used generally in one to two mols per mol of the amino compound used to acylate these reactive derivatives of carboxylic acid. The reaction temperature can be in the range of from −50° to 100° C., and the reaction time can be in the range of from about several tens of minutes to six hours. Other suitable reaction conditions may be employed, depending upon the type and reactivity of the reactants, the scale of the reaction, the type of solvent used, etc. After the reaction, the compound is separated and recovered by a conventional method as described, for example, in *Cephalosporins and Penicillins Chemistry and Biology*, Chapters 4 to 6, Academic Press (1972).

The compound of the formula (II) obtained by the above peptide bond forming reaction is a valuable antibacterial agent by itself. But if a compound of the formula (II) wherein $R_5'$ is an alkanoyloxy group is taken into the human body or contacted by bacteria, the alkanoyloxy group is hydrolyzed by esterase, and the compound is easily converted to a substance of less antibacterial activity. Therefore, the compound can be rendered stable against the decomposing action of esterase, and its antibacterial activity enhanced, by replacing the alkanoyloxy group with a heterocyclic thio group by the following process.

A compound of the formula (I)

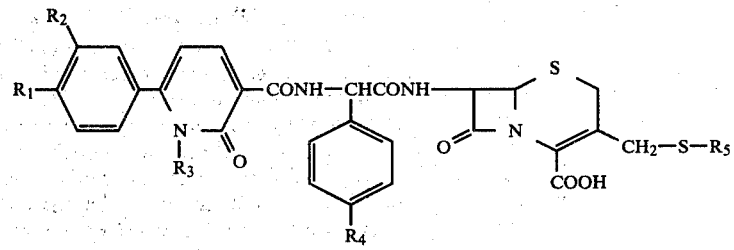

wherein $R_1$ through $R_5$ have the same meaning as defined above, can be prepared by a process wherein a compound of the formula (II) wherein $R_5'$ is a lower alkanoyloxy group is reacted with a heterocyclic thiol compound of the formula (V)

wherein $R_5$ has the same meaning as defined above.

The above reaction involves substitution reaction of the alkanoyloxy group (such as acetoxy group) bonded to the allyl position with a thiol compound and such substitution reaction is commonly used in the preparation of cephalosporins. The reaction is generally performed using from 1 to 1.5 mols of thiol compound per mol of the compound to be subtituted (e.g., a compound of the formula (II)) in a reaction medium such as water or water-containing organic solvent at a pH of about 5 to 7 and at a temperature between room temperature and about 80° C. In most cases, the reaction is substantially completed in from about several hours to ten-odd hours. For pH control, inorganic bases such as caustic alkali, alkali carbonate, alkali bicarbonate and alkali phosphate are generally used. After the reaction, the end compound is isolated in the form of a free acid or salt by a conventional method as described, for example, in the *Cephalosporins and Penicillins Chemistry and Biology*.

In the above two methods of this invention, i.e., the peptide bond forming reaction and substitution of alkanoyloxy group by a heterocyclic thiol, if functional groups such as hydroxyl group, carboxyl group, mercapto group and amino groups are present in the compounds of the formulae (II), (III) and (IV), they can be protected by known protecting methods as required, and the protecting groups are removed after the reaction as required. These protecting methods and removing method of the protecting groups are described, for example, in the *Cephalosporins and Penicillins Chemistry and Biology*, Chapters 4 to 6, Academic Press (1972).

This invention also provides a process for producing a compound of the formula (I) wherein a compound of the formula (III)

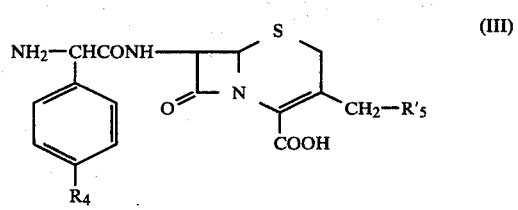

wherein $R_4$ has the same meaning as defined above, $R_5'$ represents a lower alkanoyloxy group, and the functional group (i.e., amino group) of the compound of the formula (III) is protected, is reacted with a compound of the formula (V)

wherein $R_5$ has the same meaning as defined above, to form a compound of the formula (VI)

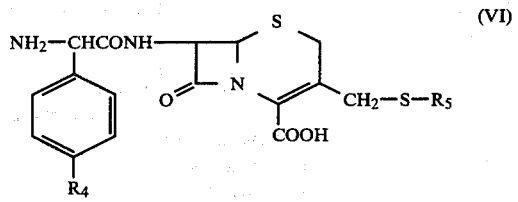

wherein $R_4$ and $R_5$ have the same meaning as defined above, and the amino group of the compound of the formula (VI) is protected;

and, after removing the protecting group according to the method as described, for example, in the *Cephalosporins and Penicillins Chemistry and Biology*, the compound of the formula (VI) is reacted with a compound (IV) having a reactive carboxyl group, said compound (IV) having the formula

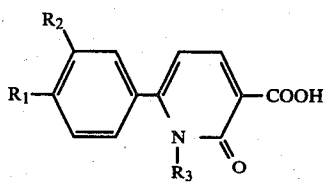

wherein $R_1$, $R_2$ and $R_3$ have the same meaning as defined above, or a compound wherein the functional groups of the compound of the formula (IV) (e.g., hydroxyl groups being present in $R_1$ and $R_2$) are protected;

and, then, if desired, the protecting groups for the functional groups (i.e., hydroxyl groups) are removed.

The compounds of the formulae (I) and (II) of this invention may also be prepared by the following method:

(i) A compound of the formula (VII)

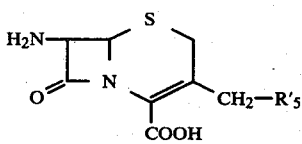

wherein $R_5'$ represents a lower alkanoyloxy group, and the carboxyl group of which is protected, is reacted with a compound of the formula (VIII)

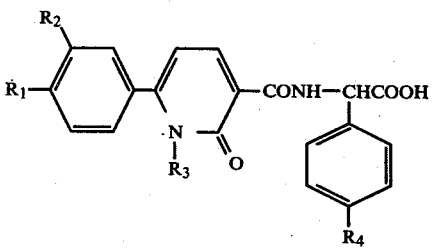

wherein $R_1$, $R_2$, $R_3$ and $R_4$ have the same meaning as defined above, or a reactive derivative at the carboxyl group of the compound of the formula (VIII) (for example, acid halide or mixed acid anhydride, etc.), under the same reaction conditions for the peptide bond forming reaction as described above, and the protecting group is then removed, to thereby obtain a compound of the formula (II). If $R_5'$ of the formula (II) is an alkanoyloxy group, the compound of the formula (II) is reacted with a heterocyclic thiol of the formula (V) to form a compound of the formula (I). The last step of substitution by a heterocyclic thiol is performed under the same reaction conditions for the reaction between the compound of the formula (II) and the compound of the formula (V) as described above.

(ii) A compound of the formula (VII)

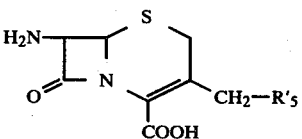

wherein $R_5'$ is a lower alkanoyloxy group, is reacted with a compound of the formula (V)

$$HS-R_5 \quad (V)$$

wherein $R_5$ has the same meaning as defined above, in the same manner for the reaction between the compound of the formula (II) and the compound of the formula (V) described above, to effect substitution by a heterocyclic thiol. After protecting the carboxyl group in the resulting compound of the formula (IX)

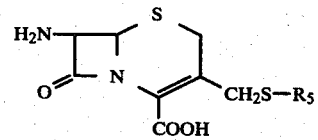

wherein $R_5$ has the same meaning as defined above, the compound is reacted: with (a) a compound of the formula (VIII) or a reactive derivative at the carboxyl group of the compound of the formula (VIII) (for example, acid halide, mixed acid anhydride, etc.); or with (b) a compound of the formula (X)

$$NH_2-CH-COOH \quad (X)$$

wherein $R_4$ is the same as defined above, or a reactive derivative at the carboxyl group of the compound of the formula (X) (for example, acid halide, mixed acid anhydride, etc.), to thereby obtain a compound of the formula (VI), the carboxyl group of which is protected. The compound formed is then reacted with the compound of the formula (IV) or a reactive derivative at carboxyl group of the compound of the formula (IV) (for example, acid halide, mixed acid anhydride, etc.), and a compound of the formula (I) results upon removal of the protecting group.

In the peptide bond forming reaction and substitution of the alkanoyloxy group by heterocyclic thiol group effected in the methods described above, if the functional groups mentioned above are present in compounds of the formulae (II), (III), (IV), (VI), (VII), (VIII), (IX) and (X), they may be protected by suitable protecting groups. For example, an amino group is suitably protected by t-butoxycarbonyl group, enamine-form protecting group, or silazane-type protecting group. A carboxyl group is protected by an alkyl ester, trichloroethyl ester, p-nitrophenyl ester, p-nitrobenzyl ester, alkanoyloxymethyl ester such as pivaloyloxymethyl ester and acetoxymethyl ester, esters such as benzhydryl ester, trityl ester and p-methoxybenzyl ester, or silyl esters. A hydroxyl group is protected by p-nitrobenzylether, p-methoxybenzylether, methoxymethylether, methoxyethylether, pyranylether or phenacylether. Further, a mercapto group is protected by a disulfide or p-nitrobenzylthioether. Other protecting groups may of course be used. The resulting reaction product with protecting groups is subjected to selective elimination of the protecting groups under mild conditions as required, or it may, as required, be used directly (without eliminating the protecting groups) as the starting material for a subsequent reaction. The condition for the selective elimination of the protecting groups varies depending on kinds of the protecting groups as described in the *Cephalosporins and Penicillins Chemistry and Biology*, Chapters 4 to 6, Academic Press (1972), and the elimination is carried out by a catalytic reduction using palladium, a reduction using zinc-acetic acid, a treatment with trifluoroacetic acid, or a treatment with trifluoroacetic acid-anisole under mild conditions which do not cause cleaving of the β-lactam ring of the compounds of the formulae (I) and (II).

The compound of the formula (I) or (II) obtained by the methods described above can be easily converted to pharmaceutically acceptable salt thereof, such as sodium salt, potassium salt, or various amine salts, by the conventional technique.

The compounds of both formulae (I) and (II) obtained by this invention are novel antibiotics which are resistant to β-lactamase (penicillinase, cephalosporinase) and have strong antibacterial activity against a wide spectrum of Gram-positive and Gram-negative bacteria, including Gram-negative bacilli typified by *Pseudomonas aeruginosa* which cannot be controlled by the conventional cephalosporin series antibiotics, such as cephalotin, cephalexin, cephaloridine and cefazolin. Table 1 shows the antibacterial spectrum of compounds according to this invention as compared with piperacillin (T-1220).

TABLE 1

Minimum Inhibitory Concentration (γ/ml) by Agar Plate Dilution Method

| Microorganisms | Compound of Example 2 | Compound of Example 5 | T-1220 |
| --- | --- | --- | --- |
| *Staphylococcus aereus* 209PJC-1 | 0.78 | 0.78 | 0.78 |
| *Staphylococcus aereus* Smith S-424 | 0.78 | 0.78 | 1.56 |
| *Bacillus anthracis* No. 119 | 1.56 | 0.20 | 0.78 |
| *Escherichia coli* GN 206 (CSase) | 3.13 | 0.20 | 25 |
| *Citrobacter freundii* GN 346 (CSase) | 3.13 | 0.78 | 100 |
| *Klebsiella pneumoniae* GN 69 (PCase) | 12.5 | 6.25 | 50 |
| *Proteus morganii* 1510 (CSase) | 25 | 12.5 | 50 |
| *Proteus rettgeri* GN 624 (CSase) | 12.5 | 3.13 | 0.78 |
| *Proteus vulgaris* OX 19 | 0.78 | 0.39 | 1.56 |
| *Serratia marcescens* No. 1 | 3.13 | 3.13 | 1.56 |
| Serratia species GN 629 (CSase) | 12.5 | 12.5 | 25 |
| *Pseudomonas aeruginosa* IAM-1007 | 6.25 | 12.5 | 12.5 |
| *Pseudomonas aeruginosa* M-0025 | 3.13 | 3.13 | 6.25 |
| *Pseudomonas cepacia* M-0527 | 6.25 | 6.25 | 1.56 |
| *Pseudomonas cepacia* TMS 199, KM 425 | 6.25 | 6.25 | — |
| Maltophilia 604 | 6.25 | 12.5 | 200 |

The compounds of this invention can be administered orally or parenterally in the form of a capsule, tablet, injection, etc. It can usually be administered advantageously as an injection. The dosage varies with age, symptom, weight, etc., and generally, an adult person would be administered a daily dosage of from about 250 to 3,000 mg, in three to four administrations. It is to be understood, however, that a larger dosage may be used, if necessary.

The toxicity of the compounds according to this invention is very low. None of the six mice administered intraperitoneally 1,000 mg/kg of the compound of Example 2 died. Therefore, the compounds of this invention have very low toxicity. In addition, they have a wide antibacterial spectrum and are very effective in treating infectious diseases, as compared with the conventional cephalosporin series antibiotics such as cephalotin, cefazolin, cephalexin and cephaloridine.

This invention is hereunder described in greater detail by the following examples and reference examples, wherein the temperatures indicated according to the Celsius scale.

REFERENCE EXAMPLE 1

(1) To a suspension of 30 g of sodium methylate in 500 ml of isopropyl ether, a solution, obtained by dissolving 90 g of 3,4-dimethoxyacetophenone in 37 g of ethyl formate while heating, was added dropwise with stirring, while cooling with ice, and the mixture was stirred at room temperature for 2 hours. The isopropyl ether was evaporated under vacuum, and the residue was dissolved in 500 ml of water. After adding 59 g of α-cyanoacetamide and 22 ml of a piperidineacetic acid buffer (pH: 8.0), the mixture was heated at 110° C. for 7 hours. While cooling, the pH of the reaction mixture was adjusted to 4.0 with acetic acid. The precipitate was filtered off, washed with 200 ml of water, recrystallized from 300 ml of ethanol, and finally washed with 100 ml of ether to obtain 41 g of 6-(3,4-dimethoxyphenyl)-3-cyano-1,2-dihydro-2-oxopyridine having a melting point of 268° to 270° C.

IR (Nujol): 2250 cm$^{-1}$ (—CN)

(2) A suspension of 41 g of 6-(3,4-dimethoxyphenyl)-3-cyano-1,2-dihydro-2-oxopyridine in 300 ml of 25% aqueous solution of potassium hydroxide was heated at 110° C. for 13 hours under stirring, and while hot, the suspension was poured into one liter of 6 N aqueous hydrochloric acid with stirring under cooling with ice. The resulting precipitate was filtered off, washed with 500 ml of water, washed three times with 300 ml of acetone, and recrystallized from dimethylformamide to obtain 41 g of 6-(3,4-dimethoxyphenyl)-1,2-dihydro-2-oxonicotinic acid having a melting point of 273° C. (with decomposition).

IR (Nujol): 1705 cm$^{-1}$ (carboxylic acid), 1632 cm$^{-1}$ (pyridone)

REFERENCE EXAMPLE 2

Synthesis of 6-[4-(3,4-dimethoxybenzyloxy)-3-methoxyphenyl]-2-oxopyridine-3-carboxylic acid

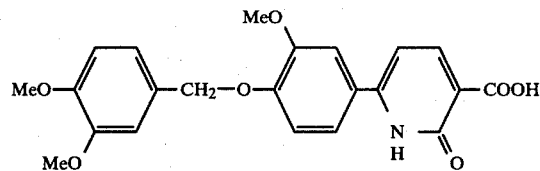

(1) To a solution of 235 g of veratryl alcohol in 1.4 liters of dry methylene chloride, 200 g of thionyl chloride was added dropwise while cooling with ice, and the mixture was stirred at room temperature overnight. The resulting dark brown reaction solution was poured into one liter of ice water. The pH of the solution was adjusted to 7.0 with sodium bicarbonate. The methylene chloride layer was separated, washed with water, dehydrated, and concentrated to dryness under vacuum to obtain 220 g of 3,4-dimethoxybenzyl chloride having a melting point of 50° to 51° C.

(2) Thirty-six grams of 60% sodium hydride was added to 200 ml of dry dimethylformamide with stirring under cooling with ice. To this solution, a second solution consisting of 120 g of acetovanillone in a 400 ml of dry dimethylformamide was added dropwise, and the mixture was stirred at room temperature for 1.5 hours. To the mixture, a solution of 200 g of 3,4-dimethoxybenzyl chloride in 400 ml of dry dimethylformamide was added dropwise, and the mixture was heated at 110° C. overnight while stirring. The dimethylformamide was distilled off under vacuum, and the residue was dissolved in 600 ml of methylene chloride, washed with 400 ml of water three times, dehydrated, concentrated to dryness, and the resulting syrup was crystallized from ethanol to obtain 16.7 g of 4-(3,4-dimethoxybenzyloxy)-3-methoxyacetophenone having a melting point of 119° to 120° C.

(3) To a suspension of 12.6 g of 60% sodium hydride in 100 ml of dry tetrahydrofuran, a solution of 50 g of 4-(3,4-dimethoxybenzyloxy)-3-methoxyacetophenone and 17.6 g of ethyl formate in 700 ml of dry tetrahydrofuran was added dropwise with stirring while cooling with ice, and the mixture was heated at 50° C. overnight while stirring. Then the tetrahydrofuran was distilled off under vacuum, and the resulting powder was dissolved in 350 ml of water. To the resulting solution, 20 g of α-cyanoacetamide and 20 ml of a piperidine-acetic acid buffer (pH: 8.0) were added, and the mixture was heated at 110° C. overnight while stirring. The reaction mixture was cooled with ice and its pH was adjusted to 4.0 with acetic acid. The solid precipitate was filtered off, washed with 300 ml of acetone and recrystallized from dimethylformamide to obtain 16.7 g of 6-[4-(3,4-dimethoxybenzyloxy)-3-methoxyphenyl]1,2-dihydro-2-oxo-3-cyanopyridine having a melting point of 220° to 221° C.

(4) A suspension of 16.7 g of 6-[4-(3,4-dimethoxybenzyloxy)-3-methoxyphenyl]1,2-dihydro-2-oxo-3-cyanopyridine in 400 ml of 25% aqueous potassium hydroxide solution was heated at 110° C. for 42 hours under stirring. The suspension was poured into 600 ml of 6 N aqueous hydrochloric acid and cooled with ice. The resulting precipitate was filtered off, washed with water and recrystallized from methyl cellosolve to obtain 10 g of 6-[4-(3,4-dimethoxybenzyloxy)-3-methoxyphenyl]-1,2-dihydro-2-oxonicotinic acid.

Melting Point: 217° to 218° C.

IR (Nujol): 1710 cm$^{-1}$ (—COOH), 1640 cm$^{-1}$ (pyridone)

REFERENCE EXAMPLE 3

Eight grams of 6-(3,4-dimethoxyphenyl)-1,2-dihydro-2-oxonicotinic acid was dissolved in 48 ml of dimethylformamide and 19 ml of pyridine. To the solution, 10 g of p-nitrophenyl trifluoroacetate was added, and the mixture was stirred at room temperature overnight. The resulting precipitate was filtered off, washed with diethyl ether, and recrystallized from dimethyl sulfoxide to give 7.9 g of p-nitrophenyl ester of 6-(3,4-dimethoxyphenyl)-1,2-dihydro-2-oxonicotinic acid.

IR (Nujol): 1700 cm$^{-1}$ (ester), 1668 cm$^{-1}$ (pyridone), 1525, 1350 cm$^{-1}$ (nitro)

REFERENCE EXAMPLE 4

To a suspension of 2.75 g of 6-(3,4-dimethoxyphenyl)-1,2-dihydro-2-oxonicotinic acid in 25 ml of dimethylformamide, 2 g of carbonyl diimidazole, and the mixture was stirred overnight at room temperature. The resulting precipitate was filtered off, and washed with ether to obtain 2.8 g of imidazole amide of 6-(3,4-dimethoxyphenyl)-1,2-dihydro-2-oxonicotinic acid.

IR (Nujol): 1690 cm$^{-1}$ (amide), 1642 cm$^{-1}$ (pyridone)

REFERENCE EXAMPLE 5

55 g of 6-(3,4-dimethoxyphenyl)-1,2-dihydro-2-oxonicotinic acid was suspended in 550 ml of methylene chloride. To the suspension, 66.6 ml of triethylamine was added, and the mixture was stirred at rroom temperature for one hour. After cooling to 5° C., 38 ml of ethyl chloroformate was added dropwise at a temperature in the range of from 0° to 10° C. After 2 hours of stirring, a solution of 46 g of N-hydroxysuccinimide in 78 ml of dimethylformamide was added dropwise, and the mixture was stirred at room temperature overnight. The resulting precipitate was filtered off, washed with water, washed with a small amount of acetone, and recrystallized from 140 ml of dimethylformamide to obtain 45 g of a succinimide ester of 6-(3,4-dimethoxyphenyl)-1,2-dihydro-2-oxonicotinic acid.

IR (Nujol): 1798, 1772 cm$^{-1}$ (amide), 1730 cm$^{-1}$ (ester), 1640 cm$^{-1}$ (pyridone)

REFERENCE EXAMPLE 6

To a suspension of 2.0 g of D-p-hydroxyphenyl glycine in 20 ml of dimethylformamide and 10 ml of water, 3.34 ml of triethylamine was added. To the mixture, 3.96 g of p-nitrophenyl ester of 6-(3,4-dimethoxyphenyl)-1,2-dihydro-2-oxonicotinic acid was added while cooling with ice. After elevating the temperature to room temperature, the mixture was stirred overnight. The solvent was distilled off under vacuum, and the resulting syrup was suspended in 50 ml of water. The pH of the suspension was adjusted to 2.0 with 1 N aqueous hydrochloric acid. The resulting precipitate was filtered off, washed with water, and recrystallized from ethanol, to obtain 4 g of 6-(3,4-dimethoxyphenyl)-1,2-dihydro-2-oxonicotinyl-p-hydroxyphenyl glycine having a melting point of 181° to 183° C. (with decomposition).

IR (Nujol): 1700 cm$^{-1}$ (carboxylic acid), 1655, 1648 cm$^{-1}$ (pyridone, amide)

REFERENCE EXAMPLE 7

To a suspension of 6 g of 6-[4-(3,4-dimethoxybenzyloxy)-3-methoxyphenyl]-1,2-dihydro-2-oxonicotinic acid in 60 ml of dimethylformamide and 10 ml of pyridine, 5 g of p-nitrophenyl trifluoroacetate was added under cooling with ice, and the mixture was stirred at room temperature overnight. The resulting precipitate was filtered off, washed with isopropyl ether, and recrystallized from dimethyl sulfoxide to obtain 6.2 g of p-nitrophenyl ester of 6-[4-(3,4-dimethoxybenzyloxy)-3-methoxyphenyl]-1,2-dihydro-2-oxonicotinic acid.

IR (Nujol): 1710 cm$^{-1}$ (ester), 1650 cm$^{-1}$ (pyridone), 1515, 1345 (nitro)

EXAMPLE 1

Six grams of p-hydroxycephaloglycine trifluoroacetate was suspended in 30 ml of dry dimethylformamide.

To the suspension, 4.2 ml of triethylamine was added with stirring while cooling with ice. To the mixture, 3.96 g of p-nitrophenyl ester of 6-(3,4-dimethoxyphenyl)-1,2-dihydro-2-oxonicotinic acid was added. After stirring at 10° C. overnight, the reaction mixture was poured into ice water, and its pH was adjusted to 1.5 with 1 N aqueous hydrochloric acid. The precipitate was filtered off, washed with water, dried and recrystalized from methanol to obtain 5.32 g of 7-{D(—)-α-[6-(3,4-dimethoxyphenyl)-1,2-dihydro-2-oxopyridine-3-carbonylamino]-p-hydroxyphenylacetamido}-3-acetoxymethyl-3-cephem-4-carboxylic acid.

IR (Nujol): 1775 cm$^{-1}$ (β-lactam), 1730 cm$^{-1}$ (acetyl), 1660 cm$^{-1}$ (amide)

EXAMPLE 2

Five grams of 7-{D(—)-α-[6-(3,4-dimethoxyphenyl)-1,2-dihydro-2-oxopyridine-3-carbonylamino]-p-hydroxyphenylacetamido}-3-acetoxymethyl-3-cephem-4-carboxylic acid was suspended in 88 ml of water, and the suspension was dissolved in 1.55 g of sodium bicarbonate. After adding 1.23 g of 5-mercapto-1-methyl-1,2,3,4-tetrazole, the mixture was heated at 65° C. for 10 hours. Passing the mixture through a resin chromatography (Diaion HP-50, a product of Mitsubishi Chemical Industries Limited) provided 1.2 g of a sodium salt of 7-{D(—)-α-[6-(3,4-dimethoxyphenyl)-1,2-dihydro-2-oxopyridine-3-carbonylamino]-p-hydroxyphenylacetamido}-3-(1-methyl-1,2,3,4-tetrazol-5-ylthiomethyl)-3-cephem-4-carboxylic acid.

IR (Nujol): 1765 cm$^{-1}$ (β-lactam), 1655 cm$^{-1}$ (amide), 1605 cm$^{-1}$ (carboxylate)

NMR (DMSO d-6) δ: 9.25 (d, 1H, NH), 8.25, 6.80 (d, 1H, pyridone ring), 7.25 (m, 3H, methoxyphenyl ring), 7.22, 6.68 (d, 2H, p-hydroxyphenyl ring), 5.65 (m, 2H, $C_7$—H, —CH—), 5.0 (dd, 1H, $C_6$—H), 4.25 (m, 2H, —$CH_2$—S), 3.90, 3.85, 3.80 (S, 3H, —O—$CH_3$—, —N—$CH_3$), 3.60 (ABq, 2H, $C_2$—H, H')

EXAMPLE 3

To a solution of 5.79 g of trifluoroacetate of 7-[D(—)-α-amino-p-hydroxyphenylacetamido]-3-(1-methyl-1,2,3,4-tetrazol-5-ylthiomethyl)-3-cephem-4-carboxylic acid in 60 ml of dry dimethylformamide, 3.2 ml of triethylamine and 5 g of p-nitrophenyl ester of 6-(3,4-dimethoxyphenyl)-1,2-dihydro-2-oxonicotinic acid were added with stirring while cooling with ice. After stirring the mixture overnight at room temperature, the insoluble matter was filtered off. The filtrate was poured into ice water, and the pH of the solution was adjusted to 1.5 with 1 N aqueous hydrochloric acid. The resulting precipitate was filtered off, washed with water, dried, dissolved in a small amount of dimethylformamide, treated with sodium 2-ethylhexanoate to form a sodium salt, and purified with a resin chromatography (HP-50), to obtain 2.6 g of the compound of Example 2.

EXAMPLE 4

To a solution of 2.12 g of 6-(3,4-dimethoxyphenyl)-1,2-dihydro-2-oxonicotinyl-D(—)-p-hydroxyphenyl glycine in 50 ml of dry tetrahydrofuran and 10 ml of dry dimethylformamide, 1.11 g of N-methylmorpholine and 1.18 g of ethyl chloroformate were added dropwise with stirring while cooling with ice. After a one-hour stirring, a solution of 2.47 g of benzhydryl 7-amino-3-(1-methyl-1,2,3,4-tetrazol-5-ylthiomethyl)-3-cephem-4-carboxylate in 20 ml of dimethylformamide was added dropwise to the mixture at a temperature between −30° C. and −10° C. The mixture was stirred for 3 hours while maintaining the temperature between −30° C. and −10° C. After stirring the mixture for one hour at a temperature between −10° C. and room temperature, the reaction mixture was poured into a mixture of chloroform and saturated sodium chloride solution under cooling with ice. After adjusting the pH of the reaction mixture to 2.0 with 1 N aqueous hydrochloric acid, the organic layer was separated, washed with water, dried, freed of the solvent by distillation under vacuum, and purified by silica gel chromatography, to obtain 3.15 g of benzhydryl ester of 7-{D(—)-α-[6-(3,4-dimethoxyphenyl)-1,2-dihydro-2-oxopyridine-3-carbonylamino]-p-hydroxyphenylacetamido]-3-(1-methyl-1,2,3,4-tetrazol-5-ylthiomethyl)-3-cephem-4-carboxylic acid.

To a mixture of 12 ml of trifluoroacetic acid and 1.2 ml of anisole cooled with ice, 1.2 g of the compound obtained was added. After stirring the mixture for one hour while cooling with ice, isopropyl ether was added, and the resulting precipitate was filtered off, washed with isopropyl ether, suspended in methanoldichloromethane, treated with sodium 2-ethylhexanoate to obtain 960 mg of sodium salt of 7-{D(—)-α-[6-(3,4-dimethoxyphenyl)-1,2-dihydro-2-oxopyridine-3-carbonylamino]-p-hydroxyphenylacetamido}-3-(1-methyl-1,2,3,4-tetrazol-5-ylthiomethyl)-3-cephem-4-carboxylic acid.

EXAMPLE 5

To a solution of 7.4 g of sodium salt of 7-[D(—)-α-amino-p-hydroxyphenylacetamido]-3-(1-methyl-1,2,3,4-tetrazol-5-ylthiomethyl)-3-cephem-4-carboxylic acid in 80 ml of dry dimethylformamide, 5.44 g of p-nitrophenyl ester of 6-[4-(3,4-dimethoxybenzyloxy)-3-methoxyphenyl]-1,2-dihydro-2-oxonicotinic acid was added while cooling with ice. After reaction at 10° C. for 30 hours, the insoluble matter was filtered off, and the filtrate was poured into ice water, and the pH was adjusted to 2.0 with 1 N aqueous hydrochloric acid. The resulting precipitate was filtered off, washed with water, washed with methylene chloride and ether, suspended in methanol-methylene chloride, and treated with sodium 2-ethylhexanoate, to obtain 5.6 g of sodium salt of 7-{D(—)-α-[6-[4-(3,4-dimethoxybenzyloxy)-3-methoxyphenyl]-1,2-dihydro-2-oxopyridine-3-carbonylamino]-p-hydroxyphenylacetamido}-3-(1-methyl-1,2,3,4-tetrazol-5-ylthiomethyl)-3-cephem-4-carboxylic acid.

IR (Nujol): 1760 cm$^{-1}$ (β-lactam), 1660 cm$^{-1}$ (amide), 1600 cm$^{-1}$ (carboxylate)

NMR (DMSO d-6) δ: 9.20 (d, 1H, NH), 8.20, 7.05 (d, 1H, pyridone ring), 7.30 (m, 10H, methoxybenzyloxy, methoxyphenyl, p-hydroxyphenyl ring), 5.70 (m, 2H, $C_7$—H, —CH—), 5.0 (d, 1H, $C_6$H)

EXAMPLES 6 TO 12

The procedures of Examples 1 to 3 were repeated to prepare compounds of formula (Ia) below wherein $R_1$, $R_2$, $R_3$, $R_4$, and R had the following meanings.

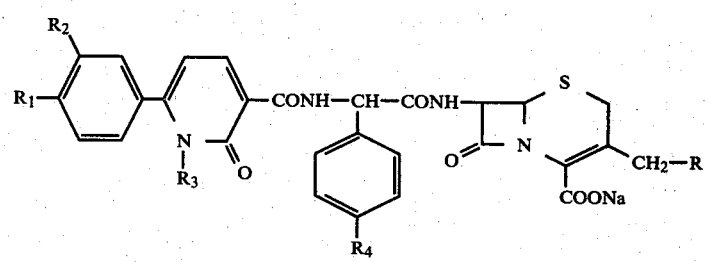

(Ia)

| Example | $R_1$ | $R_2$ | $R_3$ | $R_4$ | R | I.R. |
|---|---|---|---|---|---|---|
| 6 | —OCH$_3$ | —OCH$_3$ | H | OH | ![tetrazole]—S—C(=N-N=C-CH$_2$COONa)-N(CH$_3$)- | 1760 (β-lactam), 1660 (amide), 1600 (carboxylate) |
| 7 | —OH | H | H | OH | —OCOCH$_3$ | 1760, 1730, 1660, 1605 |
| 8 | —OH | H | H | OH | -S-tetrazole-N-CH$_3$ | 1760, 1655, 1600 |
| 9 | —OCH$_3$ | —OCH$_3$ | H | OH | -S-tetrazole-N-CH$_2$COONa | 1757, 1655, 1600 |
| 10 | —OCH$_2$-C$_6$H$_5$ | —OCH$_3$ | H | OH | —OCOCH$_3$ | 1760, 1720, 1660, 1600 |
| 11 | —OCH$_2$-C$_6$H$_5$ | —OCH$_3$ | H | OH | -S-tetrazole-N-CH$_3$ | 1755, 1655, 1600 |
| 12 | —OCH$_3$ | —OCH$_3$ | H | OH | -S-tetrazole-N-CH$_2$SO$_3$Na | 1755, 1655, 1600 |

While the invention has been described in detail and with reference to specific embodiments thereof, it will be apparent to one skilled in the art that various changes and modifications can be made therein without departing from the spirit and scope thereof.

What is claimed is:
1. A cephalosporin compound of the formula (I)

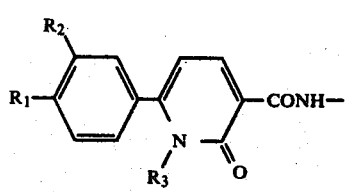

(I)

-continued

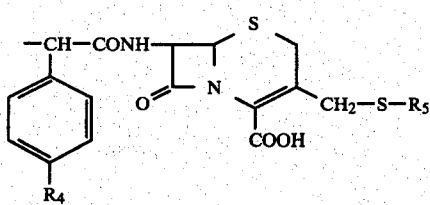

wherein $R_1$ represents a methoxy group or a 3,4-dimethoxybenzyloxy group; $R_2$ represents a methoxy group; $R_3$ represents a hydrogen atom; $R_4$ represents a hydroxyl group; and $R_5$ represents

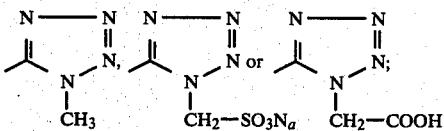

or a pharmaceutically acceptable salt thereof.

2. 7-{D(−)-α-[6-(3,4-dimethoxyphenyl)-1,2-dihydro-2-oxopyridine-3-carbonylamino]-p-hydroxyphenylacetamido}-3-(1-methyl-1,2,3,4-tetrazol-5-ylthiomethyl)-3-cephem-4-carboxylic acid or a pharmaceutically acceptable salt thereof according to claim 1.

3. An antibacterial pharmaceutical composition containing an effective amount of a compound of claim 1 and a pharmaceutically acceptable carrier.

* * * * *